United States Patent
Krueger et al.

(10) Patent No.: US 12,257,026 B2
(45) Date of Patent: Mar. 25, 2025

(54) COMBINED OPTICAL IMAGE GENERATOR AND OPTICAL IMAGING SYSTEM

(71) Applicant: KONINKLIJKE PHILIPS N.V., Eindhoven (NL)

(72) Inventors: Sascha Krueger, Hamburg (DE); Jan Hendrik Wuelbern, Hamburg (DE); Peter Forthman, Sandesneben (DE)

(73) Assignee: Koninklijke Philips N.V., Eindhoven (NL)

( * ) Notice: Subject to any disclaimer, the term of this patent is extended or adjusted under 35 U.S.C. 154(b) by 761 days.

(21) Appl. No.: 17/602,451

(22) PCT Filed: Apr. 9, 2020

(86) PCT No.: PCT/EP2020/060111
§ 371 (c)(1),
(2) Date: Oct. 8, 2021

(87) PCT Pub. No.: WO2020/208123
PCT Pub. Date: Oct. 15, 2020

(65) Prior Publication Data
US 2022/0211272 A1 Jul. 7, 2022

(30) Foreign Application Priority Data
Apr. 11, 2019 (EP) .................................... 19168610

(51) Int. Cl.
*A61B 5/00* (2006.01)
*A61B 5/055* (2006.01)
(Continued)

(52) U.S. Cl.
CPC .......... *A61B 5/0035* (2013.01); *A61B 5/0059* (2013.01); *A61B 5/055* (2013.01);
(Continued)

(58) Field of Classification Search
CPC ..... A61B 5/0035; A61B 5/0059; A61B 5/055; A61B 5/1128; A61B 5/486; G01R 33/283;
(Continued)

(56) References Cited

U.S. PATENT DOCUMENTS 3,800,149 A 3/1974 Wentworth
4,901,141 A 2/1990 Costello
(Continued)

FOREIGN PATENT DOCUMENTS

DE 102013002400 A1 8/2014
JP 2010252970 A 11/2010
(Continued)

OTHER PUBLICATIONS

Talataisong et al. "Novel method for manufacturing optical fiber: extrusion and drawing of microstructured polymer optical fibers from a 3D printer", Optics Express (Year: 2018).*

(Continued)

*Primary Examiner* — Christopher L Cook

(57) ABSTRACT

Disclosed is a medical imaging system (100, 400) component comprising: an optical image generator (122) configured for generating a two-dimensional image (200); an optical imaging system (126) configured for acquiring optical image data (166); and an optical waveguide bundle (124) comprising a subject end (132) and an equipment end (130). The subject end comprises at least one lens (136, 136). The optical image generator is configured for optically coupling to the equipment end to form an image projection pathway. The optical waveguide bundle is configured for projecting the two-dimensional image through the image projection pathway. The optical imaging system is configured for optically coupling to the equipment end to form an optical image data acquisition pathway. The optical imaging system is configured for acquiring the optical image data through the lens via the optical image data acquisition pathway.

17 Claims, 6 Drawing Sheets

(51) Int. Cl.
*A61B 5/11* (2006.01)
*G01R 33/383* (2006.01)
*G01R 33/385* (2006.01)
*G02B 6/06* (2006.01)
*G02B 23/26* (2006.01)

(52) U.S. Cl.
CPC ............ *A61B 5/1128* (2013.01); *A61B 5/486* (2013.01); *G01R 33/383* (2013.01); *G01R 33/385* (2013.01); *G02B 6/06* (2013.01); *G02B 23/26* (2013.01)

(58) Field of Classification Search
CPC ................ G01R 33/383; G01R 33/385; G01R 33/4808; G02B 23/2492; G02B 23/26; G02B 6/06
See application file for complete search history.

(56) References Cited

U.S. PATENT DOCUMENTS

| | | | |
|---|---|---|---|
| 5,414,459 A | 5/1995 | Bullwinkel | |
| 8,201,997 B1 * | 6/2012 | Salour | A61B 1/00097 374/161 |
| 10,542,913 B2 | 1/2020 | Olesen et al. | |
| 10,888,714 B2 | 1/2021 | Dempsey et al. | |
| 2012/0143040 A1 | 6/2012 | Goswami et al. | |
| 2013/0093866 A1 | 4/2013 | Ohchues et al. | |
| 2013/0201485 A1 | 8/2013 | Guivernau et al. | |
| 2014/0378816 A1 | 12/2014 | Oh et al. | |
| 2015/0200996 A1 | 7/2015 | Ziarati | |
| 2015/0372378 A1 | 12/2015 | Anderson et al. | |
| 2016/0228005 A1 | 8/2016 | Bammer et al. | |
| 2019/0143145 A1 * | 5/2019 | Laurence, Jr. | A61B 34/10 600/1 |
| 2020/0205664 A1 * | 7/2020 | Ho | A61B 5/1455 |

FOREIGN PATENT DOCUMENTS

| | | |
|---|---|---|
| JP | 2018042892 A | 3/2018 |
| JP | 2018175024 A | 11/2018 |
| WO | 2017168681 A1 | 5/2017 |

OTHER PUBLICATIONS

International Search Report and Written Opinion from PCT/EP2020/060111 mailed May 25, 2020.

* cited by examiner

COMBINED OPTICAL IMAGE GENERATOR AND OPTICAL IMAGING SYSTEM

CROSS REFERENCE TO RELATED APPLICATIONS

This application is a U.S. national phase application of International Application No. PCT/EP2020/060111 filed on Apr. 9, 2020, which claims the benefit of EP application Ser. No. 19/168,610.4 filed on Apr. 11, 2019 and is incorporated herein by reference.

TECHNICAL FIELD

The invention relates to medical imaging systems specifically magnetic resonance imaging system. Even more specifically, the invention relates to the construction of medical imaging systems and even more specifically to the construction of magnetic resonance imaging systems.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Time dependent magnetic gradient fields and radio frequency (RF) fields are used to perform a spatially dependent manipulation the orientation of the spins. Electronic components and conductive components can interact with the magnetic and radio frequency fields.

United States patent application publication US 2013093866A1 discloses an optical motion tracking system for determining the movement of an object at least partly located in a volume of difficult access and/or at least partly located in an electromagnetic field, said system comprising a borescope for imaging a pattern on the object or a surface part of the object with a camera, said pattern or surface part located adjacent to a distal end of the borescope and said camera attached to a proximal end of said borescope, and image processing means for calculating the movement of said pattern or surface part relative to the distal end of the borescope based on a plurality of frames/images captured by the camera. The invention further relates to the use of a borescope for motion tracking of an object and a marker plate suitable for use in the motion tracking system.

SUMMARY OF THE INVENTION

The invention provides for a medical imaging system component and a medical imaging system in the independent claims. Embodiments are given in the dependent claims.

In various medical imaging modalities, it may be beneficial to both image the subject as well as provide the subject with visual information. For example, movement of the subject can be monitored using an optical imaging system and then the subject can be provided with feedback that helps the subject maintain a proper positioning or hold his or her breath. Embodiments may provide for an improved method of both imaging a subject and providing the subject with two-dimensional images. This may be achieved by using an optical wave guide bundle that couples to both an optical image generator and an optical imaging system. The same optical wave guide is used for both tasks. This may have the benefit of being able to move both systems away from the medical imaging system. This is particularly beneficial for imaging modalities like magnetic resonance imaging.

In one aspect the invention provides for a medical imaging system component that comprises an optical image generator that is configured for generating a two-dimensional image. The optical image generator could for example be a display, a screen, projector or other device which is capable of generating a two-dimensional image. The medical imaging system component further comprises an optical imaging system that is configured for acquiring optical image data. The optical imaging system could for example be a camera, an infra-red camera, or other imaging system. The medical imaging system component further comprises an optical waveguide bundle that comprises a subject end and an equipment end. The subject end comprises at least one lens. The optical image generator is configured for optically coupling to the equipment end to form an image projection pathway. The optical waveguide bundle is configured for projecting the two-dimensional image through the image projection pathway. In some cases, this is through the lens in other cases the two-dimensional is projected directly through individual waveguides of the optical waveguide bundle.

The optical imaging system is configured for optically coupling to the equipment end to form an optical image data acquisition pathway. The optical imaging system is configured for acquiring the optical image data through the lens via the optical image data acquisition pathway. The lens is used to couple to the subject end of the optical waveguide bundle. This embodiment may be beneficial because the same optical waveguide bundle can be used for displaying an image to the subject as well as imaging the subject. This for example may make it easier or more cost effective to both monitor the subject and to provide a two-dimensional display to the subject.

In another embodiment the medical imaging system component further comprises an infra-red illuminator. The infra-red illuminator is configured for optically coupling to the equipment end. The optical imaging system is an infra-red camera. This embodiment may be beneficial because the infra-red illuminator will not interfere with the two-dimensional image that is produced for the subject. This means that the optical waveguide bundle can be used for simultaneously providing the two-dimensional image to the subject as well as illuminating the subject so that the optical imaging system is better able to image the subject.

In another embodiment the optical imaging system and the optical image generator are both coupled to the equipment end using a beam splitter. Likewise, the infra-red illuminator could also be coupled through the beam splitter.

In another embodiment at least a portion of the subject end forms a two-dimensional display for displaying the two-dimensional image. This may be beneficial because it may provide a particular location where the subject can view the two-dimensional image.

In another embodiment the medical imaging system component further comprises a subject support. The optical waveguide bundle is integrated into the subject support. This embodiment may be beneficial because the subject can be pre-positioned such that the subject is able to view the two-dimensional image as well as be imaged using the optical imaging system. This may for example be performed before the subject is inserted into the medical imaging system. In some embodiments the subject support may be detachable and comprise the components of the optical image generator, the optical imaging system, and the optical waveguide bundle. This may enable the use in multiple imaging systems.

In another embodiment the subject support comprises a support arch. The subject end is attached to the support arch. This embodiment may be beneficial because it may provide for a means of supporting the optical waveguide bundle and the subject end that is independent of a medical imaging system. This for example may allow consistent viewing by the subject as well as the movement of the subject support to multiple medical imaging systems.

In another embodiment the medical imaging system component comprises a cylindrical imaging component with a bore configured for receiving a subject. The subject end is mounted on a surface of the bore. The cylindrical imaging component could take different forms in different examples. For example, it may be a magnetic resonance imaging main magnet, a CT ring, a PET ring, a SPECT ring or other medical imaging system component. Mounting the subject end on a surface of the bore may be beneficial because it may provide for a permanent means of displaying the two-dimensional image as well as imaging a subject that is in the medical imaging system.

In another embodiment the optical image generator is outside of the bore. The optical imaging system is outside of the bore. This may be beneficial because it enables the optical image generator and the optical imaging system to be far away from for example high magnetic fields magnetic resonance imaging or to avoid taking expensive real estate within the bore of a medical imaging system.

In another embodiment the optical waveguide bundle is a three-dimensional printed optical waveguide bundle or is formed from lithographically structured foils. These may both form a convenient, compact and cost-effective means of building the optical waveguide bundle.

In another embodiment the optical waveguide bundle is formed from multiple optical fibers. This embodiment may also be convenient and inexpensive to construct.

In another aspect the invention provides for a medical imaging system that comprises the medical imaging system component according to an embodiment. The magnetic resonance imaging system further comprises a memory storing machine-executable instructions and imaging commands configured for controlling the medical imaging system to acquire the medical imaging data. The medical imaging system further comprises a processor configured for controlling the medical imaging system. Execution of the machine-executable instructions causes the processor to acquire the medical imaging data by controlling the medical imaging system with the imaging commands.

Execution of the machine-executable instructions further causes the processor to control the optical image generator to generate the two-dimensional image during the acquisition of the medical imaging data. Execution of the machine-executable instructions further causes the processor to control the optical imaging system to acquire the optical image data during the acquisition of the medical imaging data. This embodiment may be beneficial because it provides a means of both displaying an image to the subject as well as imaging the subject during the acquisition of the medical imaging data.

This for example may be used for providing feedback to a subject and assist the subject in maintaining a constant position during the acquisition of the medical imaging data. In addition, it may also enable a means of monitoring the subject and modifying the acquisition of the medical imaging data on the fly to improve its quality. For example, the position or location of the subject can be used to modify how the medical imaging system is being acquired.

In another embodiment execution of the machine-executable instructions further cause the processor to determine subject motion data from the optical image data. For example, the optical image data may be used to notice a change in the color on the surface of the subject. This for example may indicate a heartbeat. Small repetitive motions of the subject may be used to indicate breathing of the subject. In other examples the position of the body and/or limbs and/or head may be used to monitor the gross motion of the subject. All these for example may be useful in providing feedback to the subject and/or modifying how the medical image data is acquired.

In another embodiment execution of the machine-executable instructions further cause the processor to control the optical image generator to render a motion feedback indicator using the subject motion data. This embodiment may be beneficial because it may directly provide a means of showing the subject the body motion and/or position and enable the subject to better control it during the medical imaging process.

In another embodiment the optical image indicator is configured for displaying any one of the following: a breath hold indicator, a breathing state of the subject, a body position of the subject, and combinations thereof.

In another embodiment the medical imaging system further comprises a radiotherapy system configured for irradiating a target zone. Execution of the machine-executable instructions further causes the processor to receive radiotherapy control commands configured for controlling the radiotherapy system. Execution of the machine-executable instructions further causes the processor to modify the radiotherapy control commands using the subject motion data. This embodiment may be beneficial because the optical image data may be used to improve the positioning of the target zone.

In another embodiment the medical imaging system further comprises any one of the following: a magnetic resonance imaging system, a computer tomography system, a positron emission tomography system, a single photon emission tomography system, and combinations thereof. This may be beneficial because the medical imaging system component may be useful in all of these medical imaging modalities.

In another embodiment, the medical imaging system component is configured for projecting the two-dimensional image through the image projection pathway and for acquiring the optical image data through the lens via the optical image data acquisition pathway simultaneously. This may have the advantage that the motion feedback indicator can be provided to the subject in real time or with a reduced latency.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. 'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two- or three-dimensional data that has been acquired using a medical imaging scanner. A medical imaging system or scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) imaging data is an example of medical imaging data and is defined herein as being the recorded measurements of radio frequency signals emitted by atomic spins using the antenna of a Magnetic resonance apparatus during a magnetic resonance imaging scan. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
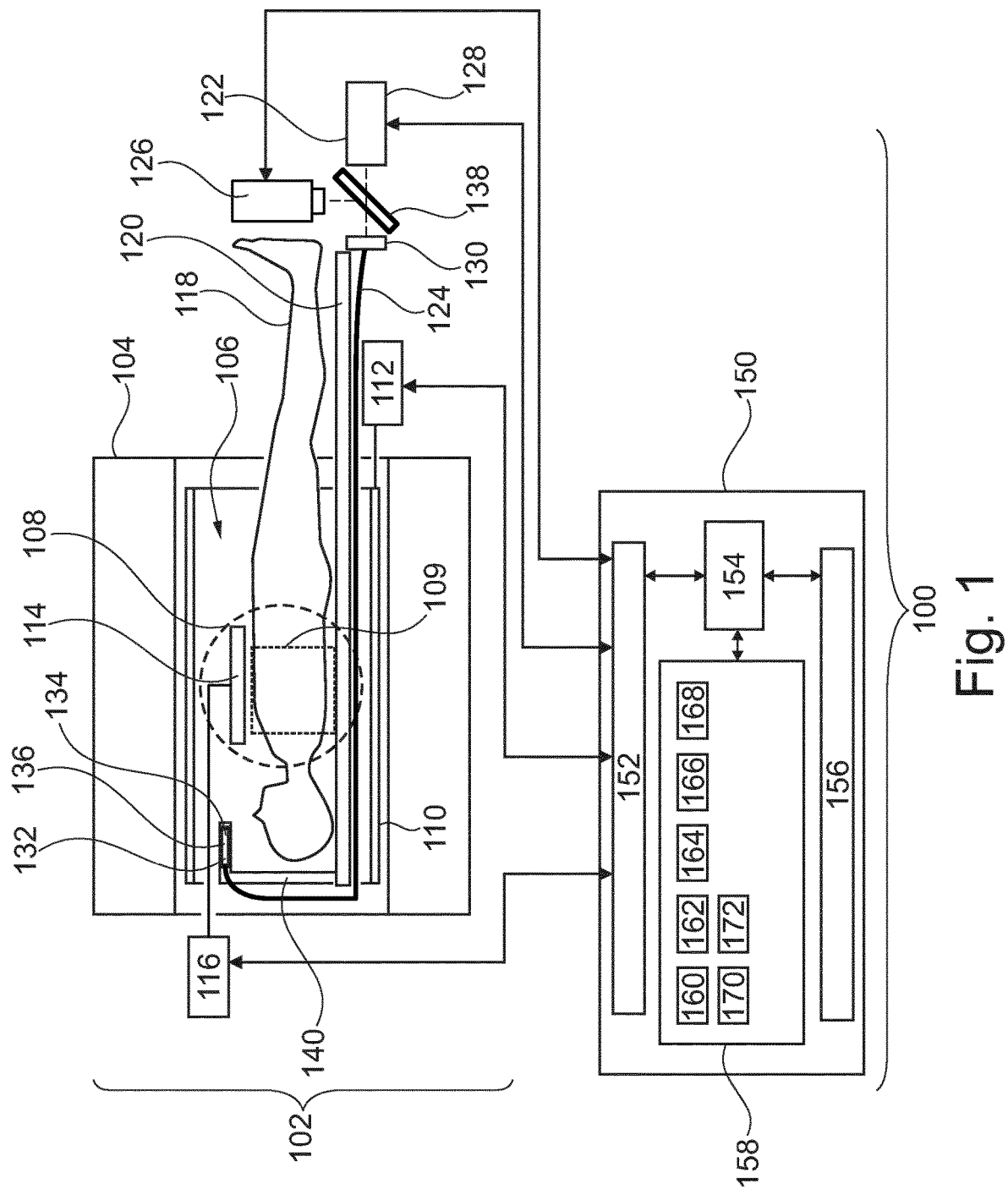
FIG. 1 illustrates an example of a magnetic resonance imaging system.
Figure 4:
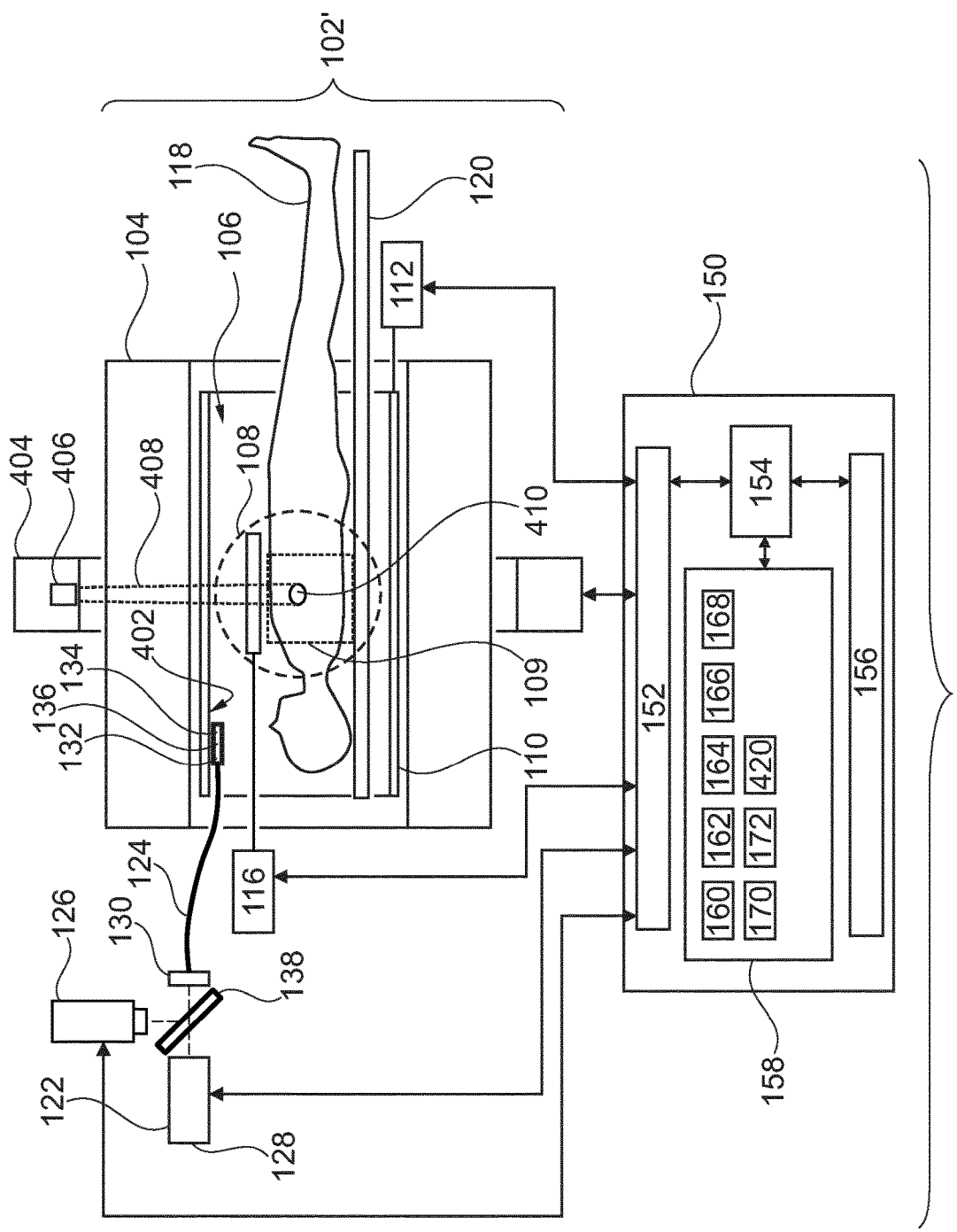
FIG. 4 illustrates a further example of a magnetic resonance imaging system.

FIG. 1 illustrates an example of a magnetic resonance imaging system 100. The magnetic resonance imaging system 100 is one example of a medical imaging system. The examples depicted in FIGS. 1 and 4 are made using magnetic resonance imaging systems. However, other medical imaging systems such as positron emission tomography systems, computer tomography systems, single photon emission tomography systems and other medical imaging systems may be substituted. The magnetic resonance imaging system 100 comprises a medical imaging system component 102 and a computer system 150.

The medical imaging system component 102 comprises a magnet 104. The magnet 104 is an example of a cylindrical imaging component. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance data that is acquired typically acquried for the region of interest. A subject 118 is shown as being supported by a subject support 120 such that at least a portion of the subject 118 is within the imaging zone 108 and the region of interest 109. Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

In this example there is an optical waveguide bundle 124 integrated into the subject support 120. The optical waveguide bundle 124 has an equipment end 130 and a subject end 132. At the equipment end 130 there is an optical imaging system 126 which may for example be a camera and an optical image generator 122. The optical image generator 122 may for example be a display or projector. The equipment end 130 may include any optical components which are necessary for coupling both the optical imaging system 126 and the optical image generator 122 to the equipment end 130. In this example a beam splitter 138 is used to couple both the optical imaging system 126 and the optical image generator 122. For optical light the optical image generator 122 may also be useful for producing illumination.

In other examples the box labeled 128 may also include an infra-red illumination system 128 and the camera or optical imaging system 126 may also be an infra-red camera. Attached to the end of the subject support 120 is a support arch 140 which supports the subject end 132 above the head of the subject 118. In some examples the subject end 132 forms a portion or a two-dimensional display 134. The subject end 132 may also contain other components such as at least one lens 136 for coupling an image of the subject 118 into the optical waveguide bundle 124. In this example the medical imaging system component 102 is shown as including the magnetic resonance imaging magnet as well as the subject support 120 and the associated objects for the optical waveguide bundle 124. In other examples the medical imaging system component 102 may just be the subject support 120 and the various optical components. This for example may enable the movement of the subject support 120 and optical components between different magnetic resonance imaging systems as well as other types of medical imaging systems.

The magnetic field gradient coil supply 112, the transceiver 116, the optical image generator 122, and the optical imaging system 126 are all shown as being coupled to a hardware interface 152 of computer system 150. The computer system 150 further comprises a processor 154 that is connected to the hardware interface 152 as well as a user interface 156 and a memory 158.

The memory 158 may be any combination of memory which is accessible to the processor 130. This may include such things as main memory, cached memory, and also non-volatile memory such as flash RAM, hard drives, or other storage devices. In some examples the memory 158 may be considered to be a non-transitory computer-readable medium.

The memory 158 is shown as containing machine-executable instructions 160. The machine-executable instructions 160 enable the processor 154 to control the operation and function of the magnetic resonance imaging system 100. The memory 158 is further shown as containing pulse sequence commands 162. The pulse sequence commands are an example of imaging commands. The pulse sequence commands 162 may be commands or data which may be converted into commands which enable the processor 154 to control the magnetic resonance imaging system 100 to acquire magnetic resonance imaging data. The memory 158 is further shown as containing magnetic resonance imaging data 164 that was acquired by controlling the magnetic resonance imaging system 100 with the pulse sequence commands 162.

The memory 158 is further shown as containing optical image data 166 that was acquired using the optical imaging system 126 during the execution of the pulse sequence commands 162. The memory 158 is further shown as containing subject motion data 168 that was derived from the optical image data 166. The memory 158 is further shown as optionally containing a motion feedback indicator 170 that was constructed using the subject motion data 168. The motion feedback indicator 170 may for example be rendered as the two-dimensional image using the optical image generator 122. The memory 158 is further shown as containing a magnetic resonance image 172 that was reconstructed from the magnetic resonance imaging data 164.

Figure 2:
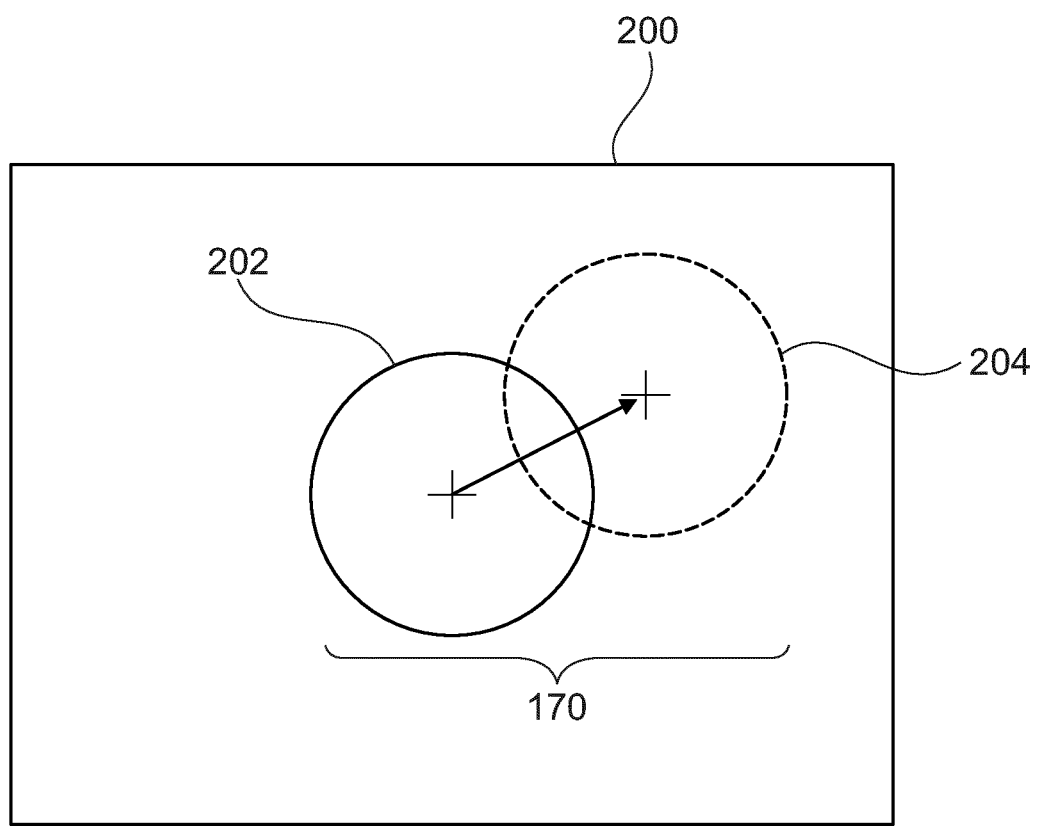
FIG. 2 illustrates an example of a motion feedback indicator.

FIG. 2 illustrates an example of a two-dimensional image 200 that may be displayed by the optical image generator 122 to the subject 118 of FIG. 1. The two-dimensional image 200 shows an example of the motion feedback indicator 170. In this example there are two circles, the first circle represents an initial position 200 and the second circle represents a current position 204. This for example may be useful in displaying different types of motion data such as repetitive breath motion and/or position. (Note to self: steal information about FIG. 2 from previous patent)

Figure 3:
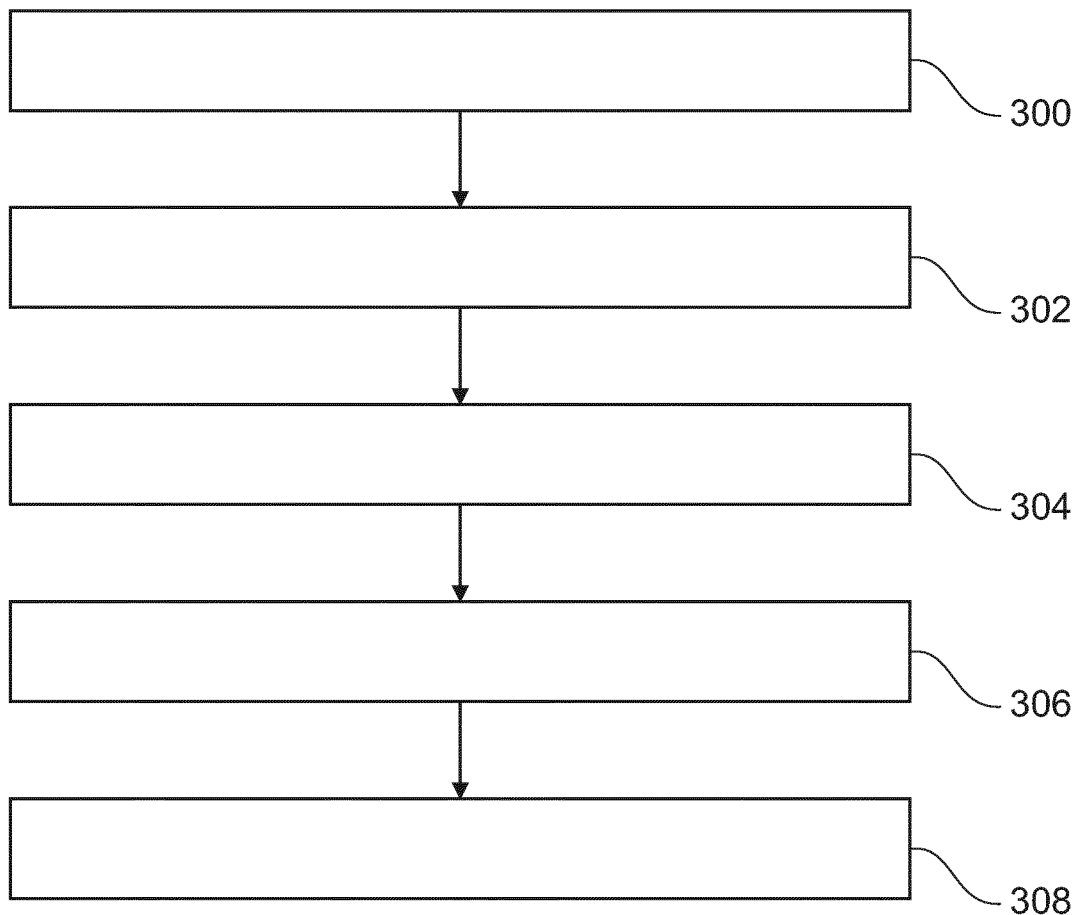
FIG. 3 shows a flow chart which illustrates a method of operating the magnetic resonance imaging system of FIG. 1.

FIG. 3 shows a flowchart which illustrates a method of operating the magnetic resonance imaging system 100 of FIG. 1. First in step 300 the medical imaging data or in this case, the magnetic resonance imaging data 164 is acquired by controlling the magnetic resonance imaging system 100 with the imaging commands. In this example the imaging commands are the pulse sequence commands 162. Next in step 302 the optical image generator is controlled to generate the two-dimensional image 200 during the acquisition of the medical imaging data 164. Next in step 304 the optical imaging system 126 is controlled to acquire the optical image data 166 during the acquisition of the medical imaging data 162. Next in step 306 the subject motion data 168 is determined from the optical image data 166. This for example may be used using such things as a neural network or also using various motion detection algorithms. Next in step 308 the optical image generator 122 is controlled to render the two-dimensional image 200 which shows the motion feedback indicator 170.

FIG. 4 shows a further example of a medical imaging system which in this case is again a magnetic resonance imaging system 400. The medical imaging system component 102' in this case is different than in FIG. 1. The equipment end 132 is mounted on a surface 402 of the bore 106 of the magnet 104. The magnet 104 is a cylindrical imaging component. The magnetic resonance imaging system 400 is further shown as comprising an optional radiotherapy system 404. The radiotherapy system 404 comprises a radiation source 406 which generates a radiation beam 408 which is able to irradiate a target zone 410. The depiction of the radiotherapy system 404 is intended to be representative and it may or may not be causing a radiation beam 408 to pass through the magnet 104. It is intended simply to indicate that the subject combination of a magnetic resonance guided radiotherapy system 404 is applicable to examples.

Figure 5:
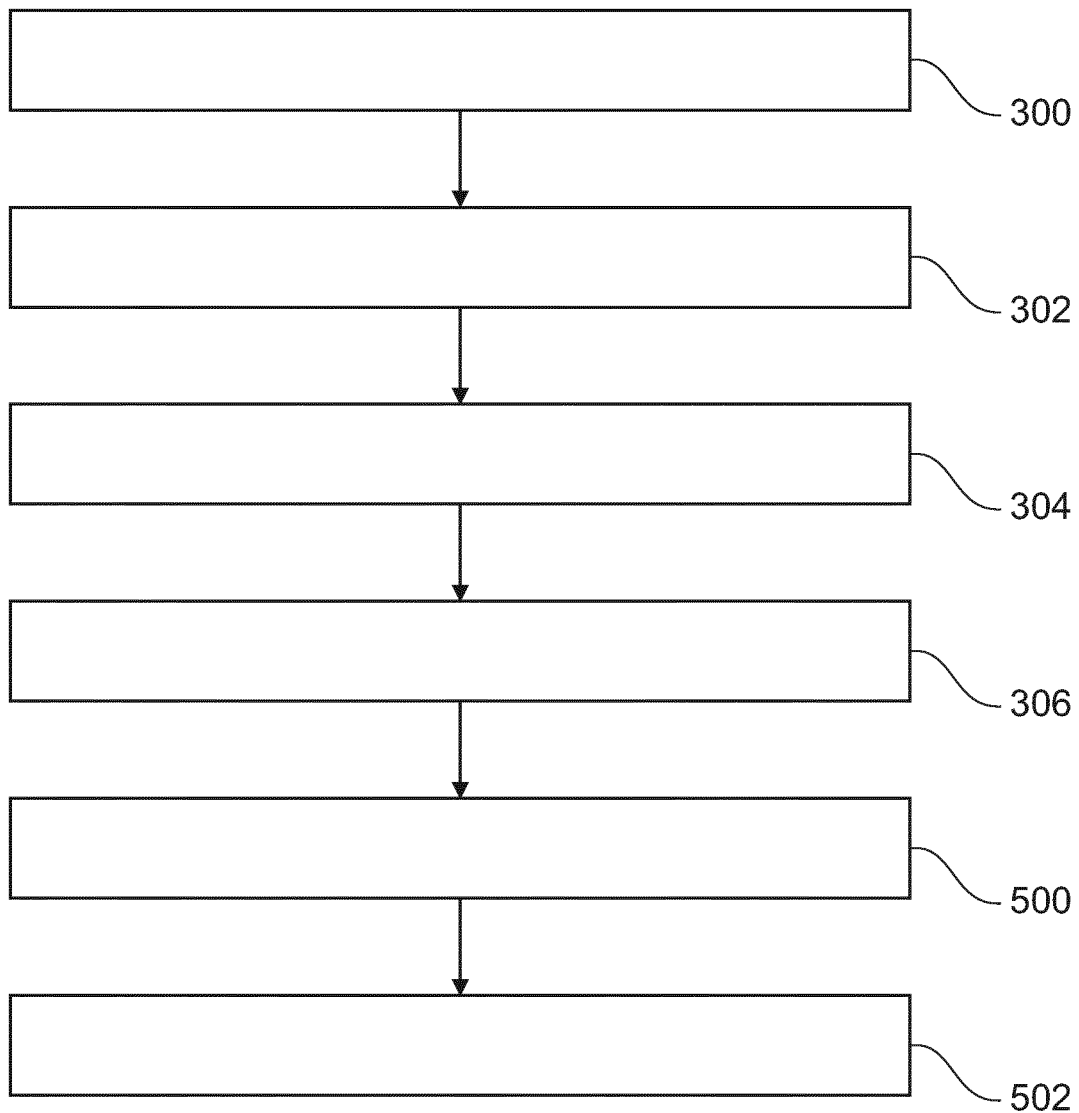
FIG. 5 shows a flow chart which illustrates a method of operating the magnetic resonance imaging system of FIG. 4.

The memory 158 is further shown as containing radiotherapy control commands 420 which are used to control the radiotherapy system 404 to irradiate the target zone 410. The magnetic resonance image 172 may of course be useful for guiding the positioning of the target zone 410. However, the magnetic resonance imaging system may not acquire data quickly enough to account for the fast motion of the subject 118. In this case the subject motion data 168 can be used to modify the radiotherapy control commands 420. FIG. 5 shows a flowchart which illustrates a method of operating the magnetic resonance imaging system 400 of FIG. 4. In FIG. 5 steps 300, 302, 304 and 306 are the same as they were performed in FIG. 3. After step 306 the method proceeds to step 500. In step 500 the radiotherapy control commands 420 are received. Then in step 502 the radiotherapy control commands are modified using the subject motion data 168.

The integration of video sensors and projection systems into a medical imaging system such as an MRI imaging system (100, 400) can be a challenge since RF interference and magnetic materials have to be avoided. This can be a major cost driver for such an integration and may also imply performance-relevant limitations in selectable hardware options. Additional integration effort is needed whenever it is desired or needed to upgrade the hardware.

Video cameras (optical imaging system 126) have been shown to be effective sensors to derive real-time physiology (e.g. breathing and pulse) and motion signals, which can be used to devise appropriate scan strategies to manage motion and improve image quality. In-bore video projection systems allow to provide guidance, feedback and entertainment to the subject to improve image quality and scanning efficiency and overall patient experience. It would be desired to have both sensors and projections systems available simultaneously, e.g. breathing may be measured and breathing instructions may be given to the patient for guidance. This may increase complexity and integration effort.

Examples may use fiber bundles (optical waveguide bundle 124) to establish a two-way optical signal path which allows to have an observation and a projection path established simultaneously. All camera, projection, data transmission, and processing electronics remain outside the RF cage inside the technical room and the optical signals are transferred via the fiber bundle towards and from the patient. Using an optical transmission system is advantageous as it is not emitting any electromagnetic interference to the MR acquisition and is simultaneously immune to gradient and RF fields generated from the MR system. Furthermore, optical fibers allow transmission and reception along the same channel, the signals are separated at the fiber bundle using a semitransparent mirror. The physiology and motion sensing pathway has a large Field of View (FOV) covering the patient torso and head and is out of focus for the eyes of the patient. The video projection pathway has a focal plane at comfortable distance and angle with respect to the subject's eyes providing a screen-like optical impression.

One example (102) would be to integrate the fiber bundle (124) with the patient support end (subject end 132) which moves along with the patient and guarantees that the video image plane and physiology/motion sensing FOV is always well positioned regardless of patient size and table position. Multiple fiber bundles or single bundles in combination with semi-transparent mirrors (beam splitter 138) can be used. If required spectral separation can be used e.g. visible video signals and IR illumination for motion detection.

Figure 6:
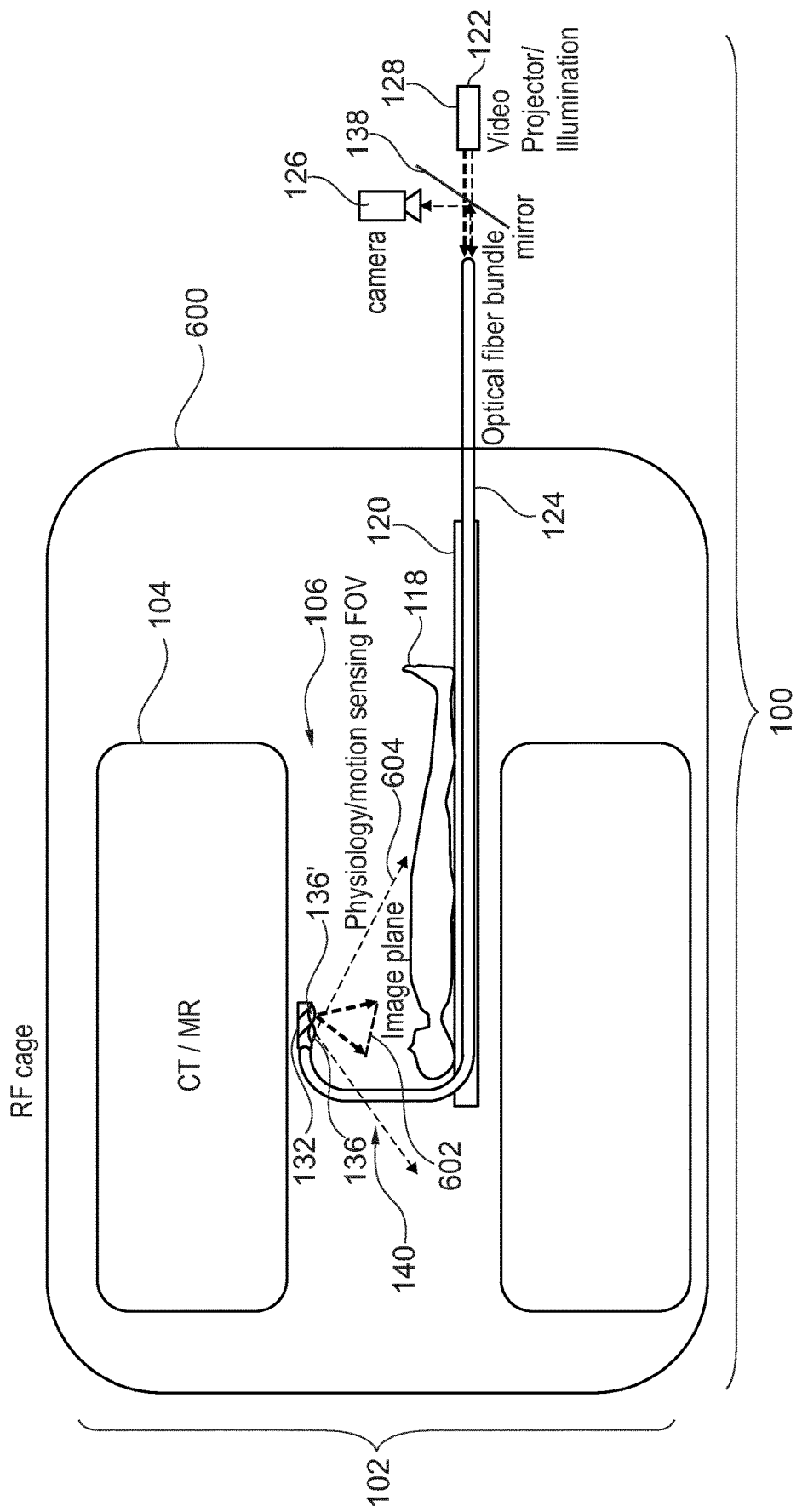
FIG. 6 illustrates a further example of a magnetic resonance imaging system.

FIG. 6 illustrates a further example of a magnetic resonance imaging system 100 wherein the optical waveguide bundle 124 is incorporated into the subject support 120. In this example there is an RF cage 600. The optical imaging system 126 and the optical image generator 122 are located outside of the RF cage 600. The equipment end 132 also is shown as having two lenses 136, 136'. One lens couples light into the optical waveguide bundle 124 and is used for guiding a physiology or motion sensing field of view 604. Another lens 136' projects light out of the optical waveguide bundle 124 and forms an image plane 602 which can be viewed by the subject 118.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
102 medical imaging system component
102' medical imaging system component
104 magnet
106 bore of magnet
108 imaging zone
109 region of interest
110 magnetic field gradient coils
112 magnetic field gradient coil power supply
114 radio-frequency coil
116 transceiver
118 subject
120 subject support
122 optical image generator
124 optical waveguide bundle
126 optical imaging system
128 optional infra-red illumination system
130 equipment end 132 subject end
134 two-dimensional display
136 lens
136' lens
138 beam splitter
140 support arch
150 computer system
152 hardware interface
154 processor
156 user interface
158 computer memory
160 machine executable instructions
162 pulse sequence commands
164 magnetic resonance imaging data
166 optical image data
168 subject motion data
170 motion feedback indicator
172 magnetic resonance image
200 two dimensional image
202 initial position
204 current position
300 acquire the medical imaging data by controlling the medical imaging system with the imaging commands
302 control the optical image generator to generate the two-dimensional image during the acquisition of the medical imaging data
304 control the optical imaging system to acquire the optical image data during the acquisition of the medical imaging data
306 determine subject motion data from the optical image data
308 render a motion feedback indicator using the subject motion data
400 magnetic resonance imaging system
402 surface
404 radiotherapy system
406 radiation source
408 radiation beam
410 target zone
420 radiotherapy control commands
500 receive radiotherapy control commands configured for controlling the radiotherapy system
502 modify the radiotherapy control commands using the subject motion data
600 RF cage
602 image plane
604 physiology/motion sensing FOV

The invention claimed is:

1. A medical imaging system comprising:
a medical imaging system component, wherein the medical imaging system component comprises:
an optical image generator configured to generate a two-dimensional image;
an optical imaging system configured to acquire optical image data; and
an optical waveguide bundle comprising a subject end and an equipment end, wherein the subject end comprises at least one lens; wherein the optical image generator is configured to optically project light representative of a two-dimensional image into the equipment end of the optical waveguide bundle for visual projection of the two-dimensional image through the at least one lens at the subject end of the optical waveguide bundle, and wherein the optical imaging system is configured to optically acquire an image through the at least one lens into the subject end of the optical waveguide bundle, the image projected into the optical imaging system through the equipment end of the optical waveguide bundle, the acquired image constituting optical image data;
wherein a same optical channel of the optical waveguide bundle is used to transmit the two-dimensional image to the subject end of the optical waveguide bundle and to transmit the acquired image to the equipment end of the optical waveguide bundle, and
wherein the medical imaging system further comprises:
a memory configured to store machine executable instructions and imaging commands configured to control the medical imaging system to acquire medical imaging data;
a processor configured to control the medical imaging system, wherein execution of the machine executable instructions causes the processor to:
acquire the medical imaging data by controlling the medical imaging system with the imaging commands; and
control the optical image generator to generate the two-dimensional image during the acquisition of the medical imaging data;
control the optical imaging system to acquire the optical image data during the acquisition of the medical imaging data;
determine subject motion data from the optical image data; and
control the optical image generator to render a motion feedback indicator using the subject motion data.

2. The medical imaging system of claim 1, wherein the medical imaging system further comprises a radiotherapy system for irradiating a target zone, wherein execution of the machine executable instructions further causes the processor to:
receive radiotherapy control commands configured for controlling the radiotherapy system; and
modify the radiotherapy control commands using the subject motion data.

3. The medical imaging system of claim 1, wherein the medical imaging system comprises one of a magnetic resonance imaging system, a computed tomography system, a positron emission tomography system, a single photon emission tomography system, and combinations any two or more thereof.

4. The medical imaging system of claim 1, wherein the medical imaging system further comprises an infra-red illuminator, wherein the infra-red illuminator is configured for optically coupling to the equipment end, and wherein the optical imaging system is an infra-red camera.

5. The medical imaging system of claim 1, wherein the optical imaging system and the optical image generator are both optically coupled to the equipment end using a beam splitter, and
wherein the light representative of the two-dimensional image is transmitted through the beam splitter from the optical image generator into the same channel at the equipment end of the optical waveguide bundle, and the image projected from the same channel at the equipment end of the optical waveguide bundle is reflected from the beam splitter to the optical imaging system.

6. The medical imaging system of claim 1, wherein at least a portion of the subject end forms a two-dimensional display for displaying the two-dimensional image.

7. The medical imaging system of claim 1, wherein the medical imaging system component further comprises a subject support, wherein the optical waveguide bundle is integrated into the subject support.

8. The medical imaging system of claim 7, wherein the subject support comprises a support arch, wherein the subject end is attached to the support arch.

9. The medical imaging system of claim 1, wherein the medical imaging system component comprises a cylindrical imaging component with a bore configured for receiving a subject, and wherein the subject end is mounted on a surface of the bore.

10. The medical imaging system of claim 9, wherein the optical image generator is outside of bore, and wherein the optical imaging system is outside of the bore.

11. The medical imaging system of claim 1, wherein the optical waveguide bundle is a three-dimensional printed optical waveguide bundle or formed from lithographically structured foils.

12. The medical imaging system of claim 1, wherein the optical waveguide bundle is formed from multiple optical fibers, and
wherein the light representative of the two-dimensional image is projected into the first ends of the multiple optical fibers at the equipment end of the optical waveguide bundle, and the two-dimensional image is projected through the at least one lens from second ends of the multiple optical fibers as the subject end of the optical waveguide bundle.

13. The medical imaging system of claim 12, wherein the image is optically acquired through the second ends of the multiple optical fibers and projected into the optical imaging system from the first ends of the multiple optical fibers.

14. The medical imaging system of claim 13, further comprising a beam splitter,
wherein the light representative of the two-dimensional image is transmitted through the beam splitter from the optical image generator into the same optical channel at the first ends of the multiple optical fibers, and the image projected from the same optical channel the first ends of the multiple optical fibers is reflected from the beam splitter to the optical imaging system.

15. The medical imaging system of claim 14, wherein a same optical channel of the multiple optical fibers is used to transmit the two-dimensional image to the subject end of the multiple optical fibers and to transmit the acquired image to the equipment end of the multiple optical fibers.

16. The medical imaging system of claim 1, wherein the medical imaging system component is configured for projecting the two-dimensional image and for acquiring the optical image data simultaneously through the same channel.

17. The medical imaging system of claim 1, wherein the at least one lens includes a first lens configured to focus light into the subject end of the optical waveguide bundle, and a second lens configured to project light from the subject end of the optical waveguide bundle.

\* \* \* \* \*